US007374766B1

(12) United States Patent
Aguilar Rubido et al.

(10) Patent No.: US 7,374,766 B1
(45) Date of Patent: May 20, 2008

(54) COMPOSITIONS CONTAINING VIRUS-LIKE PARTICLES AS IMMUNOPOTENTIATORS ADMINISTERED THROUGH THE MUCOSA

(75) Inventors: Julio César Aguilar Rubido, La Habana (CU); Daniel O. Palenzuela Gardón, La Habana (CU); Verena L. Muzio González, C. Habana (CU); Gerardo E. Guillén Nieto, C. Habana (CU); Eduardo Pentón Arias, C. Habana (CU); Dagmara Pichardo Díaz, C. Habana (CU); Enrique Iglesias Perez, C. Habana (CU)

(73) Assignee: Centro de Ingenieria Genetic y Biotechnologia, Ciudad de la Habana (CU)

(*) Notice: Subject to any disclaimer, the term of this patent is extended or adjusted under 35 U.S.C. 154(b) by 0 days.

(21) Appl. No.: 09/857,402

(22) PCT Filed: Dec. 1, 1999

(86) PCT No.: PCT/CU99/00006

§ 371 (c)(1), (2), (4) Date: Sep. 17, 2001

(87) PCT Pub. No.: WO00/32229

PCT Pub. Date: Jun. 8, 2000

(30) Foreign Application Priority Data

Dec. 2, 1998 (CU) ........................ 183/98

(51) Int. Cl.
*A61K 39/29* (2006.01)
*A61K 39/00* (2006.01)
*A61K 39/12* (2006.01)

(52) U.S. Cl. .................... 424/189.1; 424/184.1; 424/185.1; 424/186.1

(58) Field of Classification Search ............ 424/184.1, 424/225.1, 226.1, 227.1, 228.1, 192.1, 196.11, 424/199.1, 202.1, 278.1, 281.1, 193.1, 189.1; 514/44; 435/69.3, 5, 6
See application file for complete search history.

(56) References Cited

U.S. PATENT DOCUMENTS

| 4,547,368 | A | * | 10/1985 | Tabor et al. ............. 424/227.1 |
| 5,618,536 | A | * | 4/1997 | Lowy et al. ............. 424/192.1 |
| 5,840,303 | A | | 11/1998 | Chisari et al. |
| 5,932,224 | A | * | 8/1999 | Chisari .................... 424/227.1 |
| 5,962,428 | A | * | 10/1999 | Carrano et al. ................ 514/44 |
| 5,972,346 | A | * | 10/1999 | Hauser et al. ............ 424/227.1 |
| 6,025,341 | A | * | 2/2000 | Wands et al. ................. 514/44 |
| 6,048,536 | A | * | 4/2000 | Chatfield ................. 424/206.1 |
| 6,126,938 | A | | 10/2000 | Guy et al. |
| 6,153,201 | A | * | 11/2000 | Rose et al. .............. 424/204.1 |
| 6,153,392 | A | | 11/2000 | Liao et al. |
| 6,261,765 | B1 | | 7/2001 | McCarthy et al. |
| 6,319,501 | B1 | * | 11/2001 | Neurath et al. .......... 424/189.1 |
| 6,436,402 | B1 | | 8/2002 | Zhao et al. |

FOREIGN PATENT DOCUMENTS

| EP | 0 271 302 A2 | 6/1988 |
| EP | 0 534 615 A2 | 3/1993 |
| EP | 0 835 663 A2 | 4/1998 |
| EP | 0 835 663 A3 | 3/1999 |
| WO | WO 94/12617 | 6/1994 |

OTHER PUBLICATIONS

Dorland's Illustrated Medical Dictionary, 28 edition. Philadelphia, WB Saunders, 1994, p. 1787.*
Fields et al. Virology, vol. 1, 3rd edition, Philadelphia, Lippencott, Williams, and Wilkins, publishers. 1996: p. 1356.*
Lanford et al. ILAR Journal. 2001; 42 (2): 117-26, abstract only.*
Coursaget et al. Cancer Surveys. 1998; 33: 355-381, abstract only.*
Farrell. Drugs. 2000; 60 (4): 701-710.*
Fields et al. Virology, vol. 1, 3rd edition, Philadelphia, Lippencott, Williams, and Wilkins, publishers. 1996: p. 2705.*
Harrison et al. Virus Structure. In B.N. Fields et al. (ed.), Fields Virology, 3rd ed. Philadelphia: Lippincott-Raven Publishers; 1996: 60.*
Bowen et al. Research in Virology. 1992; 143 (4): 269-78, abstract only.*
Lanford et al. ILAR Journal. 2001; 42 (2): 117-26, abstract only.*
Parr Canadian Journal of Gastroenterology. 2000; 14 Suppl B: 83B-88B, abstract only.*

(Continued)

*Primary Examiner*—Zachariah Lucas
*Assistant Examiner*—Bo Peng
(74) *Attorney, Agent, or Firm*—Hoffmann & Baron, LLP (57) ABSTRACT

The present invention is related to the branch of medicine, particularly to the new formulations of vaccine antigens.

The technical objective pursued with the present invention is, precisely, the development of formulations that are able to enhance the immune response to mucosally administered antigens, minimising the number of compounds in the formulation and generating strong mucosal and systemic responses through a synergic interaction between the antigens in the formulation.

These formulations enable: a) to broaden the spectrum of the anti-hepatitis B immune response, containing as main compounds HBsAg and HBcAg, b) to enhance the response against HBsAg with a viral nucleocapsid c) to generate combined vaccines through the mucosal route with HBsAg as a central antigen. Stabilizers and preservatives can be introduced.

The formulations of this invention can be applied in the pharmaceutical industry as human or veterinary vaccine formulations.

4 Claims, 5 Drawing Sheets

OTHER PUBLICATIONS

Houghton et al. "Prospects for a vaccine against the hepatitis C virus," Nature, vol. 436, Aug. 18, 2005.*

McCluskie et al., "Immunization Against Hepatitis B Virus by Mucosal Administration of Antigen-Antibody Complexes," Viral Immunology, vol. 11, No. 4, 1998, pp. 245-252.*

Roden et al. "Preventative and therapeutic vaccines for cervical cancer," Expert Rev. of Vaccines, 2(4): 496-516 (Aug. 2003).*

Milich et al., "Antibody production to the nucleocapsid and envelope of the Hepatitis B virus primed by a single synthetic T cell site," Nature, vol. 329, pp. 547-549 (1987).*

* cited by examiner

First schedule

1- 10μg HBcAg / acemannan 3mg/mL      IN 2- 10μg HBcAg / PBS 1X      IN

3- 10μg HBcAg / alum 0.5mg/mL      SC

Fig. 1

Second Schedule

| | |
|---|---|
| 1- 10μg HBsAg/ PBS 1X | IN |
| 2- 10μg HBsAg/ acemannan 3mg/mL | IN |
| 3- 10μg HBsAg/ 10μg HBcAg / PBS 1X | IN |
| 4- 10μg HBsAg/ Alum 0.5mg/mL | SC |

Fig. 2

Third schedul

1- 5µg HBsAg / PBS 1X                IN
2- 5µg HBsAg / 5µg HBcAg             IN
3- 5µg HBsAg / 10µg HBcAg            IN
4- 5µg HBsAg / 20µg HBcAg            IN
5- 5µg HBsAg / acemannan 3mg/mL      IN
6- 5µg HBsAg / alum 0.5mg/mL         IM

Fig. 3

Fourth Schedule: Synergism at mucosal lev 1.

| | | | | | | | | |
|---|---|---|---|---|---|---|---|---|
| Acemannan 3mg/mL | X | | | X | | X | | |
| HBcAg 5μg/dose | | X | | | X | | X | |
| HBsAg 5μg/dose | X | X | X | | | X | X | |
| VLP /HPV 5μg/dose | X | X | X | X | X | | | X |

Fig. 4 Composition, per groups, in the upper part of the figure.

Fifth Schedule

1- 10µg HCV NC/ PBS 1X      IN 2- 5µg HBsAg/ PBS 1X      IN 3- 10µg HBsAg/ 10µg HCV NC / PBS 1X      IN

Fig. 5

COMPOSITIONS CONTAINING VIRUS-LIKE PARTICLES AS IMMUNOPOTENTIATORS ADMINISTERED THROUGH THE MUCOSA

TECHNICAL BRANCH

The present invention is related to the branch of medicine, particularly with the use of new vaccine immunoenhancing strategies. In this case, the adjuvant is a virus-like particle (VLP), which at the same time constitutes an antigen of interest in the formulation. The adjuvant mechanism is based on the positive effect of one antigen on others or on the synergic interaction between the antigens of the formulation.

BACKGROUND

The technical objective pursued with the present invention is, precisely, the development of formulations capable of enhancing the immune response to antigens administered through mucosal routes, minimizing the number of components in the formulation. The enhancing activity is supported by the interaction between particles at the mucosal level, generating systemic as well as mucosal immunity. Furthermore, the development of combined vaccines to the mucosal route taking as a central antigen the HBsAg, increased the immune response to one or more of coadministered antigens. The obvious advantage is the elimination of all other element or compounds different from the antigen of interest and the use of a different route. We consider that this is the basis or nucleus to develop combined vaccines for a mucosal use.

HBcAg is an extremely immunogenic antigen during the Hepatitis B Virus (HBV) infection or after immunization. In many HBV chronic patients, this is the only antigen capable of inducing an immune response. It can even induce an immune response in mice in nanogram quantities. Recently, a few structural studies have demonstrated some important characteristics explaining its potent immunogenicity. HBcAg specifically binds membrane immunoglobulin receptors in a large number of resting B cells in mice, which is sufficient to induce costimulatory B7-1 and B7-2 molecules. In this way, non-sensitised B cells, specific for HBcAg can uptake, process and present HBcAg peptides to naive T cells in vivo and to T cells hybridoma in vitro, approximately $10^5$ times more efficiently than macrophages and dendritic cells. This structure-function relationship explains the great immunogenicity of HBcAg (Milich, D. R. et al. 1997 Proc. Natl. Acad. Sci USA December 23; 94(26): 14648-53). Serologic and biochemical studies indicate that the resolution of HBV acute infection occurs in the context of an efficient cell-mediated immune response, while the chronic infection is characterized by a poor and undetectable cell-mediated immune response and a "relatively efficient" humoral response.

The humoral immunity and the cell-mediated immunity are regulated by different groups of helper T cells. Factors influencing the induction in mice of a Th1 or Th2 response to the HBV antigens (HBcAg/HBeAg) revealed that this balance was influenced (1) by the antigen structure (HBcAg is a particulated structure and HBeAg is not; (2) the major histocompatibility complex (MHC) of the host and the T cell antigens which are recognized; (3) the cross regulation between Th1 and Th2 cells; (4) the T cell tolerance, which is more complete for Th1 than for Th2 cells; (5) the activity of secreted HBeAg that preferentially delete Th1 cells (6) the treatment with cytokines, used to modulate in vivo the response toward Th1 or Th2 cells. This balance Th1/Th2 is relevant to the acute or chronic course of the HBV infection. Th2 cells preferentially evade the induction of tolerance compared with Th1. As HBeAg acts as a tolerogen during HBV vertical transmission, deleting Th1 cells, the predominance of Th2 specific cells for HBeAg could influence in the initiation and maintenance of a chronic carrier state. In this case the cytokine therapy endowed to modulate the response towards Th1, could be benefitious in the treatment of HBV chronic infection (Milich, D. R. 1997 J. Viral. Hepat.; 4 Suppl 2: 48-59).

The effect of HBeAg circulation on HBcAg Th1 specific T cells was examined by transferring HBeAg/HBcAg specific T cells to double (HBeAg and HBcAg) transgenic mice. The presence of serum HBeAg eliminated the Th1 mediated response against HBcAg and changed the balance to the Th2 phenotype. This result suggest that, in the context of the hepatitis B infection, circulating HBeAg has the potential to preferentially eliminate inflammatory specific Th1 cells needed for viral clearance, promoting the persistency of HBV (Milich-DR et al. 1998 J-Immunol. February 15; 160(4): 2013-21).

It is known that antibodies against HBcAg are present since the beginning of the infection and reach high concentrations in sera of HBV chronically infected patients, but these antibodies are not protective. Antibodies passively transmitted to newborn children by chronic carrier mothers, do not protect children of infection. (Beasley et al. 1977. American Journal of Epidemiology 105: 914-918). However, it has been demonstrated that immunizing chimps with HBcAg partially or completely protected them from HBV infection (Iwarson, S. et al. 1985 Gastroenterology 88: 763-767; Murray, K. et al. 1987 Journal of Medical Virology 23: 101-107). In Iwarson's study, three chimps were completely protected. After challenge with HBV, antibody levels against HBcAg and HBeAg increased but only one chimp seroconverted against HBsAg. In Murray's study, 2 out of 4 immunized chimps showed a low level of viral replication after challenge, HBsAg was detectable in sera for 2 or 3 weeks, and after that they developed an anti-HBsAg antibody response. It was hypothesized that the incomplete protection could be due to the low immune response in vaccinated animals without adjuvant.

After immunizing with woodchucks hepatitis core antigen (WHcAg) in Freund Complete Adjuvant (ACF), it was possible to protect woodchucks from challenge with the virus (WHV) without signs of infection detectable antibodies against the surface protein (WHsAg). Although the hypothesis that T helper anti-nucleocapsid immune response could enhance undetectable antibodies against the surface antigen can not be discarded, the cytotoxic activity was considered as the main responsible of protection (Roos, S. et al. 1989 J. Gen. Virol. 70, 2087-2095). In a second study using woodchucks the role of HBcAg and WHcAg in protection was determined as well as the possible mechanism. Animals were immunized with WHcAg and HBcAg and afterwards challenged using a high dose of WHV. In this experiment it was found that WHcAg is a protecting antigen there is a cross protection because 4 out of 6 woodchucks immunized with HBcAg were protected from the challenge. Both antigens generated a high antibody titer with a cross reactivity lower than 1%, confirming previous reports of protection using internal hepatitis B virus antigens. Since dominant B epitopes of both antigens do not appear to be conserved, this result also demonstrated that antibodies directed against core antigens are not important for protection. Woodchucks immunized with WHcAg/HBcAg reacted with a rapid response of serum antibodies against surface proteins after challenge with WHV, indicating an increased helper T cell response as a potential mechanism of protection after immunization with an internal antigen of HBV/WHV. (Schodel-F et al. Vaccine. 1993; 11(6): 624-8) Transfection of established cell lines from BALB/C mice hepatocytes with dimeric HBV DNA (ML lines) resulted in the expression of HBV antigens in these lines. The adoptive transference of spleen cells of BALB/c mice immunized with ML-1.1 cells expressing HBsAg as well as HBcAg, caused a regression of tumours cells expressing the corresponding antigens in athymic mice. Furthermore, the transfer of spleen cells of BALB/c mice immunized with HBsAg or HBcAg also caused tumoral regression. These results demonstrated that surface and nucleocapsid antigens could induce immunity capable of rejecting the hepatocellular carcinoma in vivo (Chen, S. H. et al. 1993 Cancer-Res. October 1; 53(19): 4648-51).

Therapeutic vaccines based on specific nucleocapsid epitopes for human HLA are being assayed in phase II/III studies (Liaw, Y. F. 1997 J. Gastroenterol. Hepatol. October, 12 (9-10): S227-35).

HBcAg has been demonstrated to be a very good carrier. HBcAg is a highly immunogenic antigen in human and animal models. HBcAg directly activates B cells and generates strong T cell responses. Furthermore, the efficient processing and presentation of HBcAg by the antigen presenting cells makes it an ideal carrier molecule. Hence a large number of epitopes have been chemically linked or genetically fused to the HBcAg molecule to successfully increase their immunogenicity. Bacterial expression vectors have been designed to enable the insertion of heterologous B cell epitopes in different positions inside the particles of HBcAg and the efficient purification of hybrid particles.

Positional studies of B cell epitopes demonstrated that internal insertions by the amino acid 80 continue to be immunodominant, permitting an increase in the production of antibodies as compared to other fusion proteins. Immunogenicity studies have been performed with experimental challenge in different systems. For example, a peptide from *Plasmodium berghei* Circunsporozoite was inserted in this site and the purified hybrid particle HBcAg/CS was highly immunogenic and protected 100% of challenged mice against malaria. Aimed to the development of oral vaccines, attenuated avirulent Salmonella strains have been used to introduce genes coding for hybrid particles of HBcAg (Milich, D. R. et al. 1995 Ann. N.Y. Acad. Sci. May 31; 754: 187-201).

In conclusion, apart from the relationship between HBcAg and protection, total or partially evidenced in chimps or indirectly referred by the experiments with WHcAg, this protein has a number of properties that makes it unique. HBcAg behaves as a T dependent as well as a T independent antigen (Milich, D. R. et al. 1986 Science 234, 1398-1401), it is very immunogenic, even without the help of adjuvants and its inoculation preferentially sensitises Th1 cells (Milich, D. R. et al. 1997, J. Virol. 71, 2192-2201). HBcAg is a very efficient carrier protein (Schödel, F. et al. 1992 J. Virol. 66: 106-114; Milich-DR et al. 1995 Ann-N-Y-Acad-Sci. May 31; 754: 187-20) and Th HBcAg specific cells mediate the antibody response against HBcAg as well as anti-HBsAg (Milich, D. R. et al. 1987 Nature (London) 329: 547-549). These immunologic characteristics are unique for the particulated HBcAg and do not apply to the non-particulated form of the antigen, the HBeAg (Milich, D. R. et al. 1997 Proc. Natl. Acad. Sci USA December 23; 94(26): 14648-53).

SUMMARY OF THE INVENTION

The present invention provides a vaccine formulation suitable for mucosal administration, the vaccine includes a mixture of a surface antigen from a virus, and a non-living vaccine antigen, the surface antigen having an adjuvant effect on said vaccine antigen. Each vaccine dose includes up to about 1 milligram each of the surface antigen and vaccine antigen. The vaccine formulation may include one or more of the following: a preservative, a stabilizer and a second vaccine antigen.

In a particular embodiment the surface antigen is Hepatitis B virus surface antigen (HBsAg). The vaccine antigen may an antigen of a viral nucleocapsid, such as the nucleocapsid antigen of Hepatitis B virus, the nucleocapsid antigen of Human papilloma-virus, or the nucleocapsid antigen of Hepatitis C virus.

DETAILED DESCRIPTION OF THE INVENTION

In the present invention it is reported for the first time a vaccine formulation having as main compounds: HBsAg and HBcAg in adequate proportions Other compounds may be introduced as stabilizers and preservatives.

The novelty of HBsAg/HBcAg formulation is linked to the anti HBsAg enhancing effect generated when HBsAg is mixed with HBcAg. Both antigens are compounds of HBV and hence, the role of the adjuvant is taken by other viral antigen attractive per se as a vaccine antigen, becoming a vaccine formulation with a wider anti-hepatitis B immune response spectrum. Other formulations of nucleocapsid antigens combined with surface antigens, for example the formulation HBsAg/Virus like particle of Human Papilloma Virus and extended to other viral antigens, results in an increase in titers against both antigens. After mixing HBsAg with other antigens, an increase in the immunogenicity over other coinoculated antigens could be shown, evidencing a synergic effect produced by the combination X+HBsAg through the nasal route. In general, these results enables the generation of HBsAg mucosal combined vaccines, and enables the use of the positive interactions between VLP, considering VLP as organized proteic or lipoproteic structures, resembling viruses, with a size of nanometers.

In the case of the formulation containing HBsAg and HBcAg, we can obtain a superior product as compared to the single HBsAg commercially available vaccine because:

It is possible to obtain a wider spectrum of immune response generated by HBcAg regarded as an important antigen per se in anti-HBV protection. Furthermore, the IgG seric levels anti-HBsAg reached by mucosal inoculation is as intense as the one obtained with the systemic inoculation in alum.

The route of inoculation offers special advantages such as: systemic and mucosal immunity at the same time, the elimination of strong quality controls such as sterility and pyrogens as well as the high prices of injected vaccines, the related toxicity.

The toxic effect generated by alum-based vaccines and the toxic effects of adjuvant injection can be avoided because the antigen number 2 is at the same time the adjuvant.

It is possible to use the initial HBsAg+HBcAg formulation as a nucleus of combined vaccines.

It is possible to immunize non-responders to the surface antigen and immunodepressed patients using this preparation, due to the inoculation route and the introduction of the nucleocapsid antigen regarded as a protective antigen per se.

The characteristics of this formulation make it an ideal formulation for therapeutic use.

In the second place, nucleocapsid antigens, favour the increase of coinoculated antigens immunogenicity. We found a great simplicity of resulting formulations and, at the same time, the increased valence of these potential vaccines with a minimal number of antigens due to the possibility of avoiding the use of adjuvants, which are per se non-interesting antigens for protection. In this way very reduced combinations can be obtained if desired, for single or combined vaccines.

In the third place, it is possible to generate combined vaccines having as a nucleus the HBsAg whose immunoenhancing effect on other coinoculated antigens is demonstrated in the example 4. The advantages of these formulations are based on the effective association of HBsAg, as a central antigen of the anti HBV vaccine, with other antigens, with a demonstrated synergic effect in the generated response for both antigens. This fact, not only has the attraction of previously described variants but it also makes the HBsAg, —protecting antigen for a widely distributed world disease—the central antigen of combined formulations.

In general terms, compared to other mucosal vaccines, it is possible to detach the following advantages:

- The 'adjuvation' process—mixing antigens—does not require the adsorption of antigens, and the quantity of the HBcAg antigen is at similar levels of HBsAg.
- The filtration as a sterilizing process can be used due to the small size of the particles, while other strategies and adjuvants over 0.2 μm can not be sterilized in this way.
- The simplicity of the production process for HBcAg makes it a very cheap antigen as compared to other adjuvants.

The formulations object of the present invention may present volumes from 0.01 until 10 mL, depending of the inoculation route and the species to immunize. The antigen doses vary in a range of 0.001 to 1 mg.

EXAMPLES OF PERFORMANCE

Example 1

With the aim of evaluating the immunogenicity of HBcAg through the nasal route, 3 groups of 8 female BALB/c mice were inoculated with a dose of 10 μg of HBcAg in all cases. The first group was inoculated with HBcAg in acemannan (CIGB, La Habana) 3 mg/mL (dry weight), adjuvant previously used to increase the immunogenicity of particulated systems through the nasal route. The second group was inoculated with HBcAg in phosphate-saline (PBS) buffer. Group 3 was injected subcutaneously with the antigen in alum and used as a control group for systemic inoculation. The schedule was followed of inoculations on days 0, 14, 28 and the extraction was done on day 42. The antibody response was quantified by immunoenzymatic assay (ELISA) to determine the IgG antibodies against HBcAg in sera. The Student's t test was performed to analyse statistically the results, $p<0.05$ was considered a significant difference.

It was demonstrated that, with the use of acemannan it was impossible to increase the anti-HBcAg antibody immune response. The antigen in PBS generated an immune response of a similar intensity to that obtained using acemannan (FIG. 1). The responses after nasal inoculation, in acemannan or in PBS, were similar to the response obtained using alum systemically. In conclusion, HBcAg can be used through the nasal route with a high immunogenicity.

Example 2

With the aim of demonstrating the immunoenhancing activity of HBcAg on HBsAg when both are mixed and inoculated through the nasal route, 4 groups of 8 female BALB/c mice were assayed. A two inoculations schedule was carried out. The inoculations were on days 0 and 14. The extraction was on day 21. The group 1 was inoculated with 10 μg of HBsAg in PBS, group 2 with 10 μg of HBsAg in acemannan (CIGB, La Habana) 3 mg/mL (dry weight), group 3 with 10 μg of HBsAg and 10 μg of HBcAg. Group 4 was used as a systemic control, inoculating subcutaneously 10 μg of HBsAg in alum (FIG. 2). The Student t test was performed to analyse statistically the results, $p<0.05$ was considered a significant difference.

From this experiment we concluded that it is possible to enhance the anti HBsAg immune response with the inoculation through the nasal route of HBsAg and HBcAg. The anti HBsAg response was significantly superior as compared to the group when the HBsAg was inoculated in PBS and similar to that reached by the group inoculated in acemannan. The systemic inoculation of HBsAg in alum did not differ significantly from the groups inoculated with acemannan through the nasal route.

Example 3

With the aim of studying the enhancing effect of HBcAg at different doses in the murine model, 6 groups of 6 female BALB/c mice were selected. The schedule had three inoculations (days 0, 14 and 28) and two extractions (days 26 and 42). The assayed groups corresponded with: (1) HBsAg 5 μg in PBS; (2, 3 y 4) HBsAg 5 μg with 5, 10 y 20 μg of HBcAg respectively, (5) HBsAg 5 μg in acemannan 3 mg/mL (dry weight) and (6) HBsAg 5 μg in alum 0.5 mg/mL. All groups except 6 were inoculated nasally. Group 6 was inoculated intramuscularly.

The Student's t test was used to analyse statistically the results, p<0.05 was considered a significant difference.

In this experiment we concluded again that it is possible to enhance the anti-HBsAg response with the coinoculation of HBsAg and HBcAg. The serum IgG response for the three immunized groups with both antigens was significantly higher to that obtained by inoculation of HBsAg in PBS and similar to that attained by the group inoculated in acemannan. We have demonstrated previously that acemannan increased the titers to levels similar to that obtained by cholera toxin in mice. Titers obtained by systemic inoculation in alum did not differ from that of acemannan and HBcAg/HBsAg groups by the nasal route. Although group 4 anti-HBsAg antibody response decreased as compared to group 3, the difference was due to a double increase in the HBcAg dose in-group 4. This increase might reduce the possibilities of HBsAg to penetrate mucosa.

Example 4

Different antigens were employed with the aim of studying the interaction of virus-like particles of Human Papilloma Virus 16 (VLP del VPH 16), HBsAg and HBcAg. Were immunized 8 groups of 6 female BALB/c mice with a schedule based in inoculations on days 0, 14 and the extraction 7 days after second inoculation.

Comparing antibody titers against HBsAg, the response of acemannan formulation (group 6) has the same intensity to the HBcAg/HBsAg formulation (group 7) respectively. This is the third time that we demonstrate the enhancing effect of HBcAg.

Figure 1:
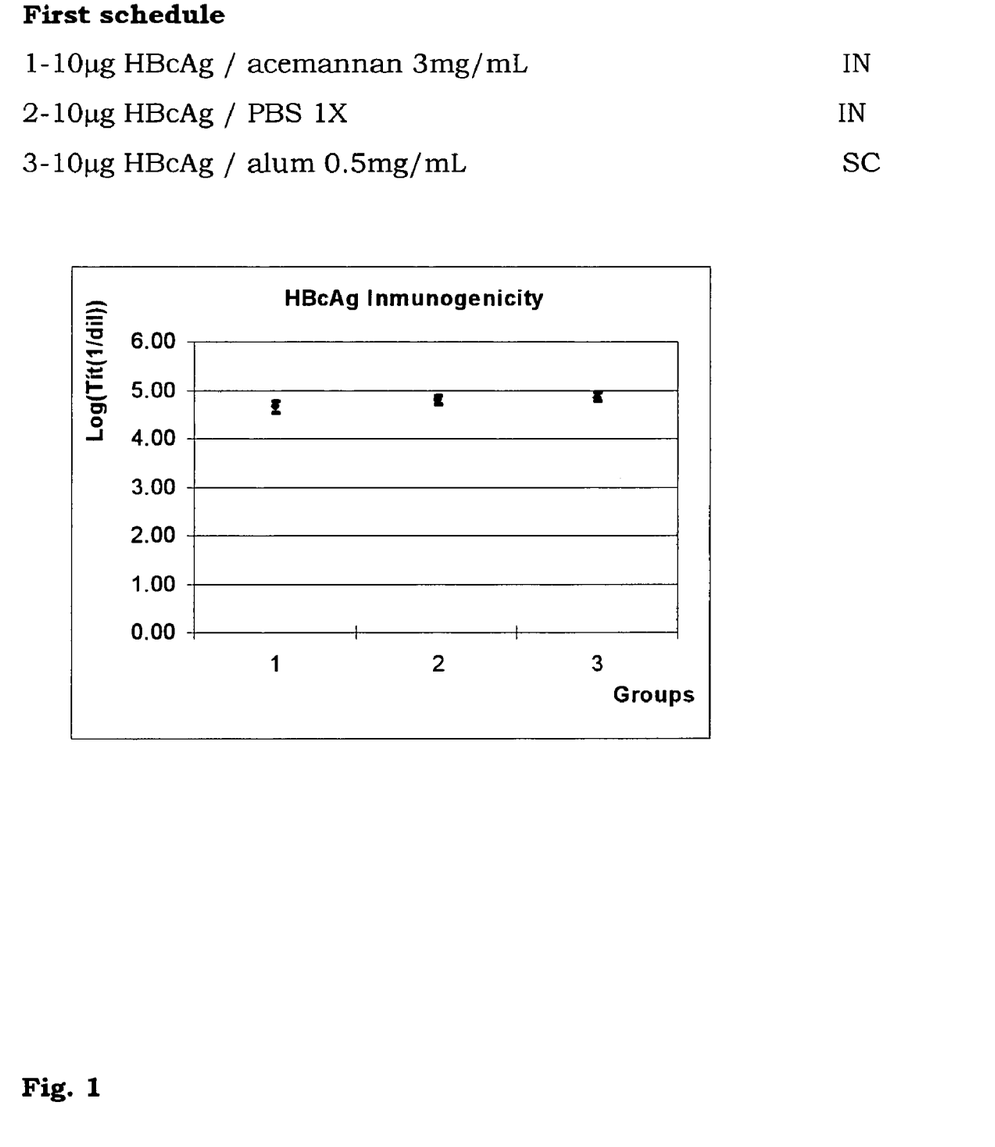
FIG. 1. Three doses schedule (days 0, 14 and 28). Extraction was performed on day 42. Groups 1 and 2 were inoculated with 50 µL through the nasal route. Group 3 was inoculated subcutaneously with 100 µL.
Figure 2:
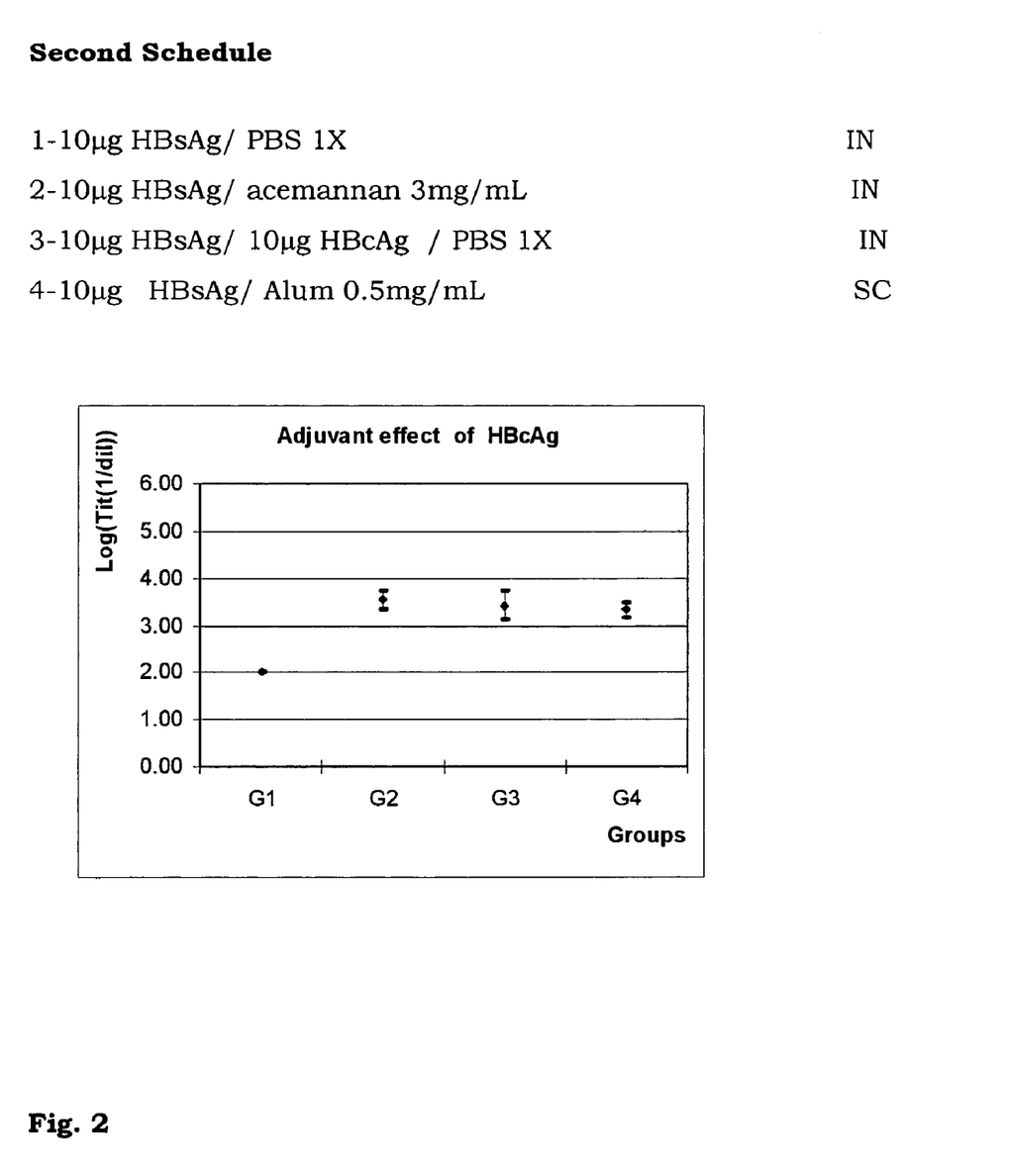
FIG. 2. Two doses schedule (days 0 and 14). Extraction was performed on day 21. Groups 1, 2 and 3 were inoculated with 50 µL through the nasal route. Group 4 was inoculated subcutaneously with 100 µL.
Figure 3:
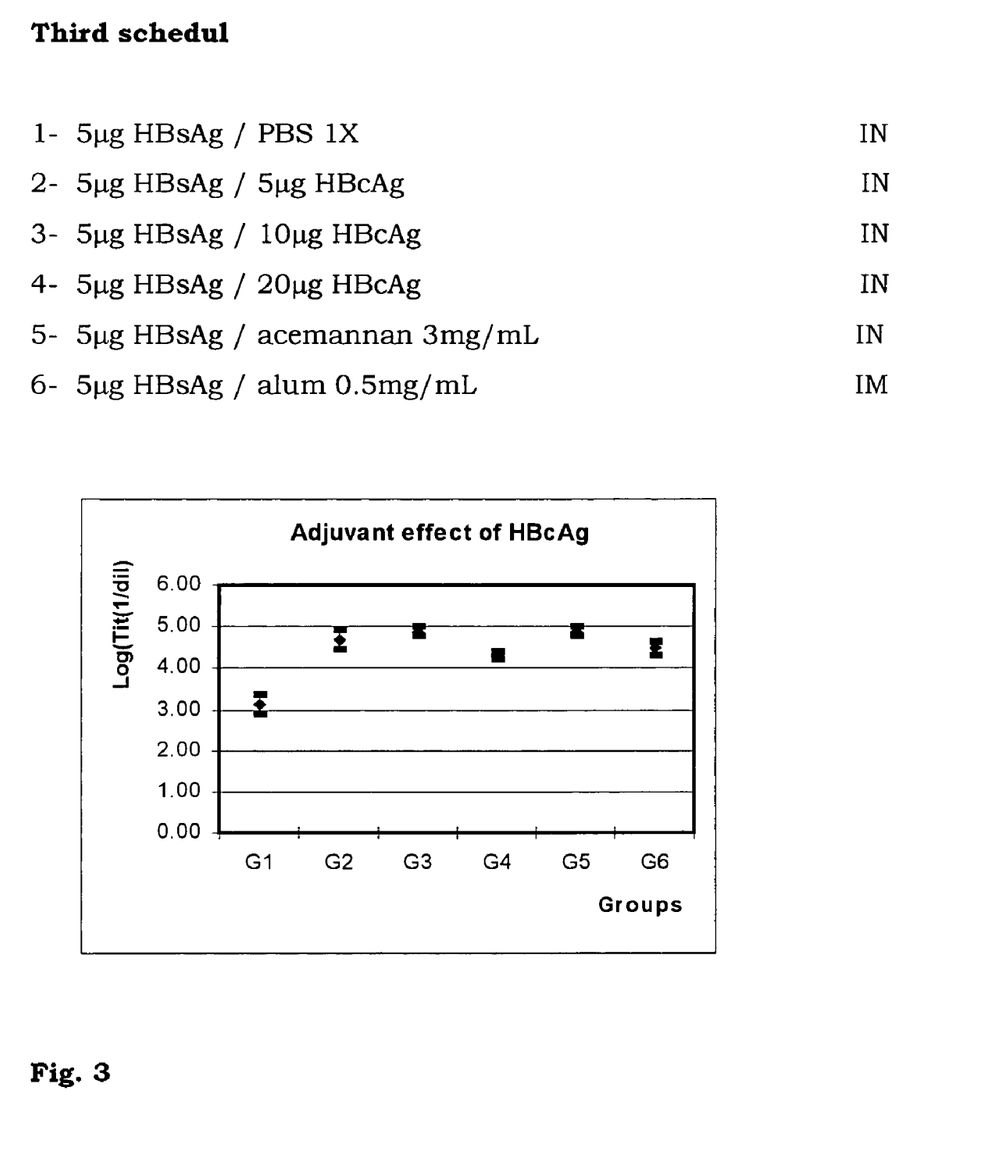
FIG. 3. Three doses schedule (days 0, 14 and 28). Extraction was performed on day 26. Groups 1, 2, 3, 4 and 5 were inoculated through the nasal route. Group 6 was inoculated intramuscularly with 100 µL.
Figure 4:
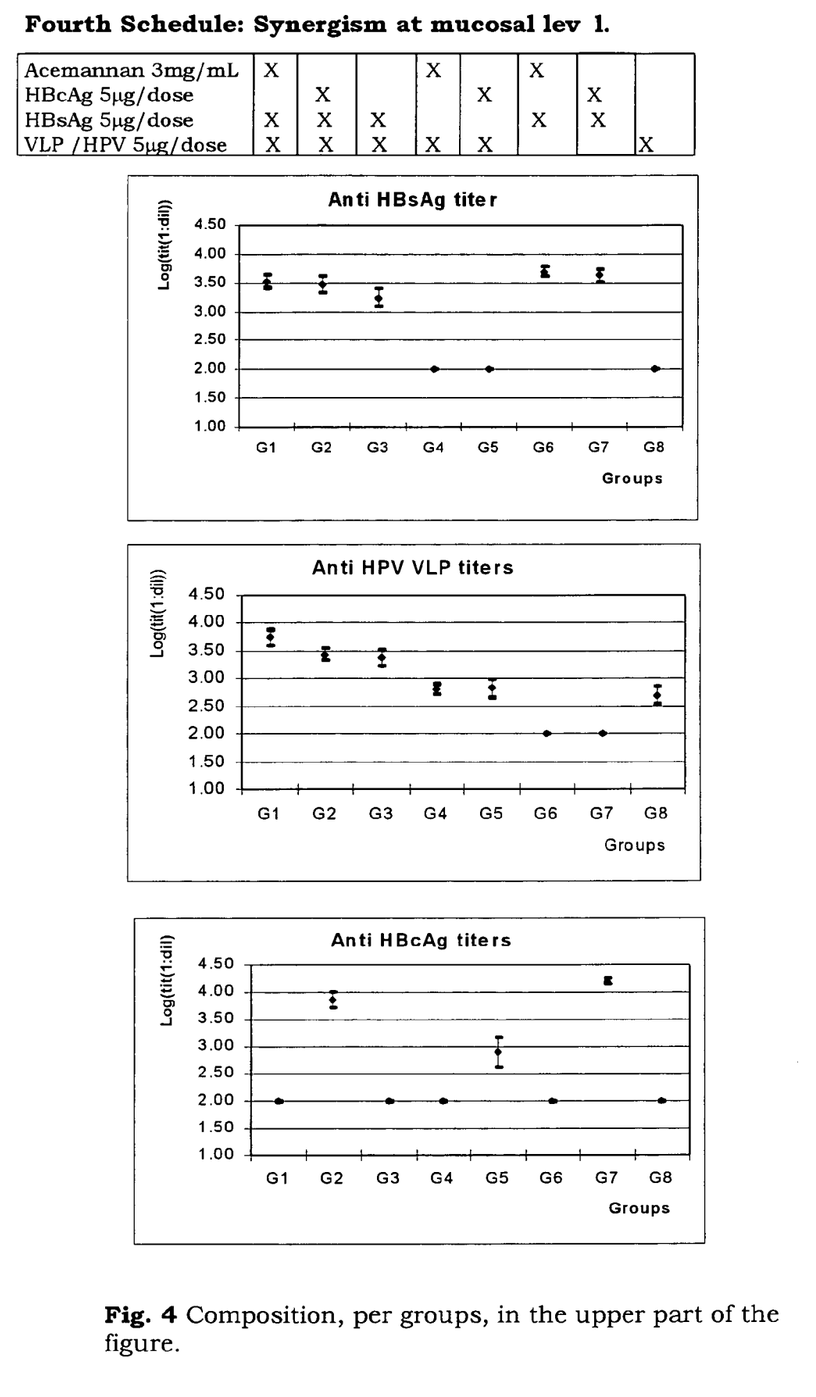
FIG. 4. Two doses schedule (days 0 and 14). Extraction was performed on day 26. All groups were inoculated nasally with 50 µL. The composition of experimental groups is shown in the table added to the figure.
Figure 5:
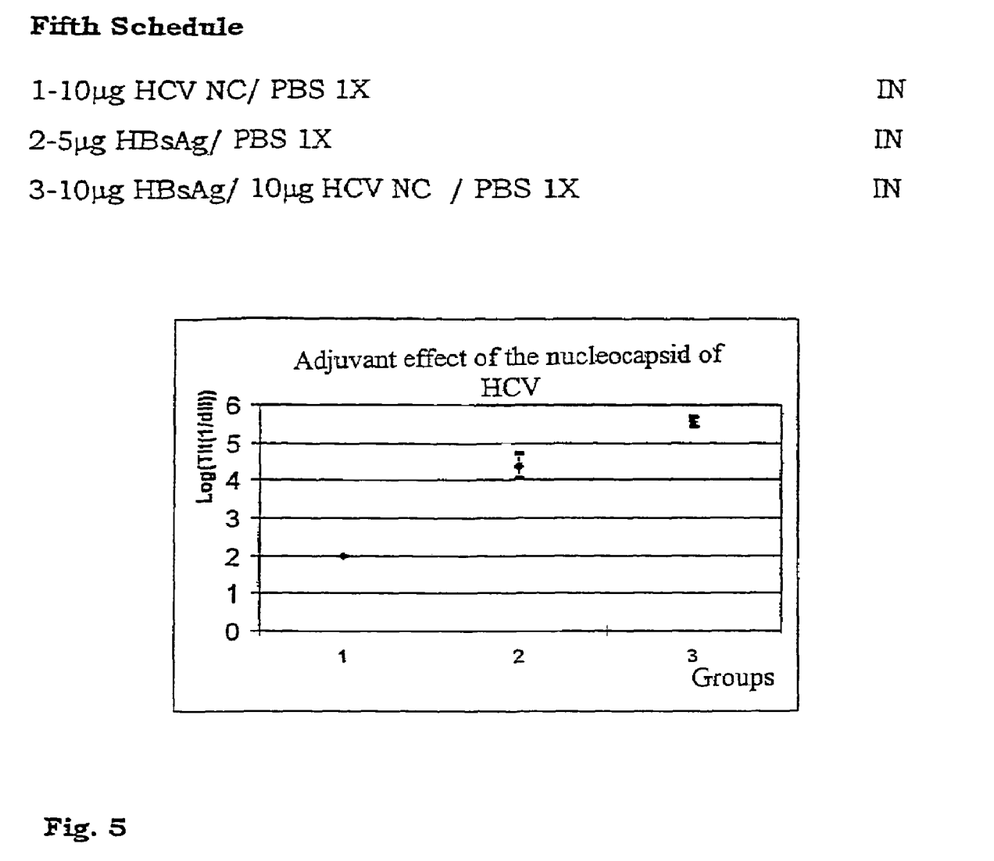
FIG. 5. Three doses schedule (days 0, 14 and 28). Extraction was performed on day 42. Groups 1, 2 and 3 were inoculated with 50 µL through the nasal route.

From this experiment we also concluded that neither acemannan nor HBcAg enhanced antibody responses against VLP of Human Papilloma Virus (HPV), represented as groups 4, 5 and 8 in the third graphic. Statistical analysis using Student's t test (p<0.05 was considered a significant difference) did not show any difference between these groups.

Analysing the response against HBcAg in the group 5, where HBcAg and VLP of HPV were inoculated, low levels of antibody titers against HBcAg could be demonstrated as compared to group 7, where HBcAg was introduced along with HBsAg. Perhaps, the presence of these two particles antagonizes at the mucosal level. However, in group 2, high anti HBcAg and anti VLP of HPV could be achieved with the addition of HBsAg, being significantly higher the increase in these responses as compared to group 5 and do not differ from anti HBcAg response of group 7 (along with HBsAg). Hence we could realize a positive interaction between HBsAg and core antigens and a negative interaction between VLPs and HBcAg. The enhancing effect at mucosal level can occur in both senses, enabling the design of combined vaccines having as a nucleus HBsAg or the HBsAg/HBcAg combination.

HBsAg effect on group 2 not only enhanced the response against HBcAg, but it also enhanced the antibody response against the VLP of HPV. The same effect can be appreciated comparing the response against VLP between groups 1, 2 and 3 with group 8 where VLP were inoculated in PBS. Groups 1, 2 and 3 had statistically similar antibody levels, all of them higher than the group 8 level.

Group 1 (acemannan+HBsAg+VLPs HPV) and group 3 (HBsAg and VLP), did not differ in anti-HBsAg antibody titers. There was no statistical difference between group 3 and groups 6 and 7 (HBsAg/Acemannan and HBsAg/HBcAg respectively). This result evidenced the enhancing effect of VLP of HPV on HBsAg immunogenicity.

These results support the use of combined formulations through nasal routes with HBsAg as a central immunoenhancing antigen. For example, the simple mixture of HBsAg and HPV VLP is very attractive and makes real the possibility of introducing more antigens, enhanced by the interaction with HBsAg.

The creation of complex formulations is possible without reduction of antibody response against each component, for example: VLP of HPV, HBcAg and HBsAg can be mixed without affecting IgG response against each component.

Example 5

With the aim of demonstrating the immunoenhancing activity of Hepatitis C Virus Nucleocapsid (HCV NC) on HBsAg when both are mixed and inoculated through the nasal route, 3 groups of 8 female BALB/c mice were assayed. A two inoculations schedule was carried out. The inoculations were on days 0, 14 and 28. The extraction was on day 42. The Group 1 was inoculated with 10 μg of HCV NC, group 2 was inoculated with 5 μg of HBsAg in PBS and group 3 with 5 μg of HBsAg and 10 μg of HCV NC in PBS (CIGB, La Habana) (FIG. 5).

The Student t test was performed to analyse statistically the results, $p<0.05$ was considered a significant difference.

From this experiment we concluded that it is possible to enhance the IgG response with the mucosal (IN) coadministration of HBsAg and HCV NC. The IgG serum response was significantly higher compared to the group immunized with HBsAg in PBS.

The invention claimed is:

1. An immunogenic composition comprising a mixture of:
(a) a first antigen which is Hepatitis B virus surface antigen (HBsAg), and
(b) a second antigen selected from the group consisting of Hepatitis C virus core antigen and a virus-like particle of Human Papilloma virus type 16,
wherein said HBsAg has an adjuvant effect on the second antigen, and wherein said first and second antigens are each present from 0.001 mg to 1 mg.

2. The composition according to claim 1, wherein the composition is suitable for nasal administration.

3. An immunogenic composition comprising a mixture of:
(a) a first antigen which is Hepatitis B virus surface antigen (HBsAg), and
(b) a second antigen and a third antigen, wherein the second and third antigens are selected from the group consisting of Hepatitis C virus core antigen, Hepatitis B core antigen (HBc) and a virus-like particle of Human Papilloma virus type 16,
wherein the antigens are each present from 0.001 mg to 1 mg, wherein the HBsAg has an adjuvant effect on the second or third antigen.

4. A method for generating an immune response in a mammal comprising administering mucosally to the mammal an immunogenic composition, wherein the immunogenic composition comprises a mixture of:
(a) a first antigen which is Hepatitis B virus surface antigen (HBsAg), and
(b) a second antigen is selected from the group consisting of Hepatitis C virus core antigen, Hepatitis B core antigen (HBc) and a virus-like particle of Human Papilloma virus type 16,
wherein said HBsAg has an adjuvant effect on the second antigen, and wherein said first and second antigen are each present from 0.001 mg to 1 mg.

* * * * *